United States Patent
Sang et al.

(10) Patent No.: US 10,508,071 B2
(45) Date of Patent: *Dec. 17, 2019

(54) METHOXYCARBONYLATION WITH FORMIC ACID AND METHANOL

(71) Applicant: EVONIK DEGUSSA GMBH, Essen (DE)

(72) Inventors: Rui Sang, Liaocheng (CN); Jie Liu, Solna (SE); Kaiwu Dong, Bo Zhou (CN); Ralf Jackstell, Rostock (DE); Matthias Beller, Ostseebad Nienhagen (DE); Robert Franke, Marl (DE)

(73) Assignee: EVONIK DEGUSSA GMBH, Essen (DE)

( * ) Notice: Subject to any disclaimer, the term of this patent is extended or adjusted under 35 U.S.C. 154(b) by 0 days.

This patent is subject to a terminal disclaimer.

(21) Appl. No.: 16/043,644

(22) Filed: Jul. 24, 2018

(65) Prior Publication Data
US 2019/0047936 A1  Feb. 14, 2019

(30) Foreign Application Priority Data

Aug. 8, 2017 (EP) .................................... 17185366

(51) Int. Cl.
*C07C 67/04* (2006.01)
*C07C 67/38* (2006.01)
*B01J 31/24* (2006.01)

(52) U.S. Cl.
CPC .............. *C07C 67/04* (2013.01); *C07C 67/38* (2013.01); *B01J 31/2409* (2013.01); *B01J 2231/321* (2013.01); *B01J 2531/824* (2013.01); *B01J 2540/40* (2013.01)

(58) Field of Classification Search
CPC ...................................................... C07C 67/04
USPC ............................................................ 560/243
See application file for complete search history.

(56) References Cited

U.S. PATENT DOCUMENTS

| | | | |
|---|---|---|---|
| 3,488,383 A | 1/1970 | Coffey et al. | |
| 2011/0137059 A1* | 6/2011 | Eastham | ............... C07F 9/5027 556/22 |
| 2014/0255296 A1 | 9/2014 | Beller et al. | |

OTHER PUBLICATIONS

U.S. Appl. No. 16/043,621, filed Jul. 24, 2018, Rui Sang et al.
U.S. Appl. No. 16/043,657, filed Jul. 24, 2018, Rui Sang et al.
Search Report dated Mar. 19, 2019 for Singapore Patent Application No. 10201806668X (2 pages).
Dong, K. et al. Palladium-Catalyzed Carbonylation of sec- and tert-Alcohols. Angewandte Chemie International, 2017, 56, pp. 6203-6207.
Sang, R., et al. Palladium-Catalyzed Selective Generation of CO from Formic Acid for Carbonylation of Alekenes. Journal of the American Chemical Society. 2018. vol. 140. pp. 5217-5223.

* cited by examiner

*Primary Examiner* — Ana Z Muresan
(74) *Attorney, Agent, or Firm* — Smith, Gambrell & Russell, LLP

(57) ABSTRACT

Process for methoxycarbonylation with formic acid and methanol.

12 Claims, No Drawings

METHOXYCARBONYLATION WITH FORMIC ACID AND METHANOL

BACKGROUND OF THE INVENTION

Field of the Invention

The invention relates to a process for methoxycarbonylation with formic acid and methanol.

Description of Related Art

The methoxycarbonylation of alkenes is a process of increasing importance. In classical methoxycarbonylation an olefin is reacted with CO and MeOH in the presence of a catalyst comprising a ligand and a metal:

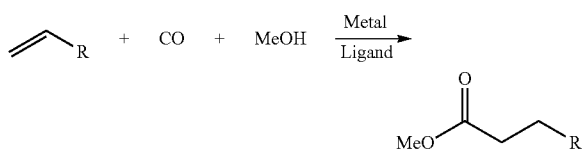

CO is introduced into the reaction vessel as a gas.

BRIEF SUMMARY OF THE INVENTION

It was an object of the invention to provide a process that employs a CO source other than CO gas which is introduced into the reaction vessel. The process should achieve a high yield of methyl ester.

The object is achieved by the process, which follows.

Process comprising the process steps of:
a) addition of an olefin;
b) addition of a compound comprising Pd, wherein the Pd is capable of forming a complex;
c) addition of a compound of general formula (I):

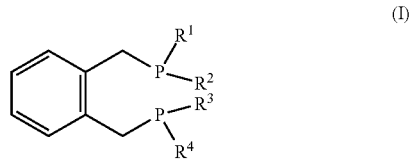

wherein $R^1$, $R^2$, $R^3$ and $R^4$ are each independently selected from: -H, -($C_1$-$C_{12}$)-alkyl, —O—($C_1$-$C_{12}$)- alkyl, -($C_4$-$C_{14}$)-aryl, -O-($C_4$-$C_{14}$)-aryl, cycloalkyl, -($C_1$-$C_{12}$)-heteroalkyl, -O-($C_1$-$C_{12}$)-heteroalkyl, —($C_3$-$C_{14}$)-heteroaryl, -O-($C_3$-$C_{14}$)-heteroaryl, -COO-alkyl, -COO-aryl, -C-)alkyl, -C-O-aryl, $NH_2$, halogen and the residues are also capable of forming a larger condensed ring; wherein the recited alkyl groups, aryl groups, cycloalkyl, heteroalkyl groups, heteroaryl groups may be substituted as follows:
-($C_1$-$C_{12}$)-alkyl, -O-($C_1$-$C_{12}$)-alkyl, halogen; and at least one of the radicals $R^1$, $R^2$, $R^3$, $R^4$ does not represent phenyl;
d) addition of MeOH;
e) addition of HCOOH,
wherein the employed volume based on 2 mmol of olefin is in the range from 0.3 ml to 0.8 ml;
f) heating of the reaction mixture to convert the olefin into the methyl ester.

DETAILED DESCRIPTION OF THE INVENTION

In one variant of the process no CO gas is supplied to the reaction mixture.

In one variant of the process HCOOH serves as the only CO source for the reaction.

In one variant of the process the compound in process step b) is selected from:
Pd(acac)$_2$, PdCl$_2$, Pd(dba)$_3$*CH$_3$Cl (dba=dibenzylideneacetone), Pd(OAc)$_2$, Pd(TFA)$_2$, Pd(CH$_3$CN)Cl$_2$.

In one variant of the process the compound in process step b) is Pd(OAc)$_2$.

In one variant of the process the process comprises the additional process step g): g) addition of an acid.

In one variant of the process, the acid is selected from: $H_2SO_4$, $CH_3SO_3H$, $CF_3SO_3H$, PTSA (p- toluenesulfonic acid).

In one variant of the process the acid is PTSA (p-toluenesulfonic acid).

In one variant of the process the employed volume of HCOOH based on 2 mmol of olefin is in the range from 0.4 ml to 0.6 ml.

In one variant of the process $R^1$, $R^2$, $R^3$, $R^4$ are each independently selected from: -($C_1$-$C_{12}$)-alkyl, -O-($C_1$-$C_{12}$)-alkyl, -($C_4$-$C_{14}$)-aryl, -O-($C_4$-$C_{14}$)-aryl, cycloalkyl, -($C_1$-$C_{12}$)-heteroalkyl, -O-($C_1$-$C_{12}$)- heteroalkyl, -($C_3$-$C_{14}$)-heteroaryl, -O-($C_3$-$C_{14}$)-heteroaryl, -COO-alkyl, -COO-aryl, -C-O-alkyl, -C—O-aryl, $NH_2$, halogen and the residues are also capable of forming a larger condensed ring; wherein the recited alkyl groups, aryl groups, cycloalkyl, heteroalkyl groups, heteroaryl groups may be substituted as follows:
-($C_1$-$C_{12}$)-alkyl, -O-($C_1$-$C_{12}$)-alkyl, halogen; and at least one of the radicals $R^1$, $R^2$, $R^3$, $R^4$ does not represent phenyl.

In one variant of the process $R^1$, $R^2$, $R^3$, $R^4$ are each independently selected from: -($C_1$-$C_{12}$)-alkyl, -($C_4$-$C_{14}$)-aryl, cycloalkyl, -($C_1$-$C_{12}$)-heteroalkyl, -($C_3$-$C_{14}$)-heteroaryl, halogen and the residues are also capable of forming a larger condensed ring;
wherein the recited alkyl groups, aryl groups, cycloalkyl, heteroalkyl groups, heteroaryl groups may be substituted as follows:
-($C_1$-$C_{12}$)-alkyl, -O-($C_1$-$C_{12}$)-alkyl, halogen; and at least one of the radicals $R^1$, $R^2$, $R^3$, $R^4$ does not represent phenyl.

In one variant of the process $R^1$, $R^2$, $R^3$, $R^4$ are each independently selected from: -($C_1$-$C_{12}$)-alkyl, cycloalkyl, -($C_3$-$C_{14}$)-heteroaryl and the residues are also capable of forming a larger condensed ring;
wherein the recited alkyl groups, cycloalkyl, heteroaryl groups may be substituted as follows:
-($C_1$-$C_{12}$)-alkyl, -O-($C_1$-$C_{12}$)-alkyl, halogen, and at least one of the radicals $R^1$, $R^2$, $R^3$, $R^4$ does not represent phenyl.

In one variant of the process $R^1$, $R^4$ are each independently selected from: -($C_1$-$C_{12}$)-alkyl, cycloalkyl, and the residues are also capable of forming a larger condensed ring;
wherein the recited alkyl groups, cycloalkyl may be substituted as follows:
-O-($C_1$-$C_{12}$)-alkyl, halogen.

In one variant of the process $R^2$, $R^3$ each independently represent -($C_3$-$C_{14}$)-heteroaryl, wherein the recited heteroaryl groups may be substituted as follows:
-O-($C_1$-$C_{12}$)-alkyl, halogen.

In one variant of the process the compound of general formula (I) has the structure (II):

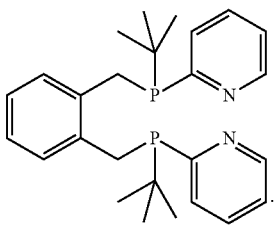

(II)

The invention is more particularly elucidated hereinbelow with reference to exemplary embodiments.

Pd-catalyzed methoxycarbonylation of tetramethylethylene 1a with HCOOH: Effect of employed volume of HCOOH

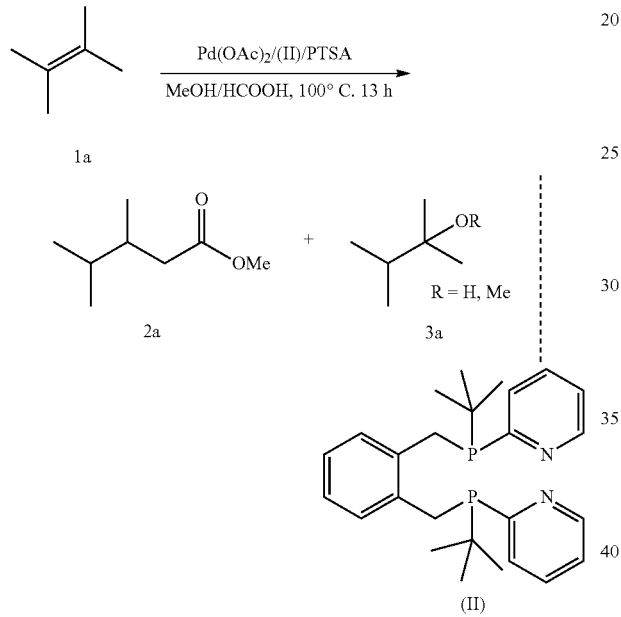

Added to a sealed 35 ml tube were [Pd(OAc)$_2$] (1.12 mg, 0.25 mol%), (II) (8.72 mg, 1.0 mol%), p-toluenesulfonic acid (PTSA.H$_2$O) (15.2 mg, 4 mol %) and an oven-dried stirrer rod. The tube together with the lid were placed into a long Schlenk tube having a large opening. The Schlenk tube is evacuated three times and refilled with argon. Under an argon atmosphere 1a (2 mmol), MeOH (1.5 ml) and HCOOH (X ml) (X see table 1) were injected into the 35 ml tube using a syringe. The 35 ml tube was then sealed with the lid. The reaction was carried out at 100° C. over 13 h. At the end of the reaction the tube was allowed to reach room temperature without additional cooling and carefully decompressed. Isooctane (100 µl) was then injected as internal standard. Conversion was measured by GC analysis.

The results are summarized in table 1 which follows:

TABLE 1

| HCOOH (volume in ml) | Conversion % | Yield of 2a % | Yield of 3a % |
|---|---|---|---|
| 0.2 | 73 | 53 | 17 |
| 0.3 | 85 | 72 | 11 |
| 0.5 | 91 | 80 | 7 |
| 0.8 | 90 | 71 | 5 |

As is shown by the experiments described above, the problem is solved by a process according to the invention.

The invention claimed is:

1. A process for the methoxycarbonylation of alkenes to form a methyl ester of an acid that corresponds to the alkene comprising the process steps of:
   a) adding an olefin to form a reaction mixture;
   b) introducing to the mixture a compound comprising Pd, wherein the Pd is capable of forming a complex;
   c) introducing to the mixture a compound of general formula (I):

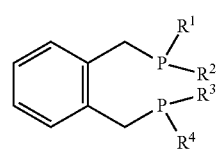

(I)

wherein $R^1$, $R^2$, $R^3$ and $R^4$ are each independently selected from the group consisting of: -H, -(C$_1$-C$_{12}$)-alkyl, -O-(C$_1$-C$_{12}$)-alkyl, -(C$_4$-C$_{14}$)-aryl, -O-(C$_4$-C$_{14}$)-aryl, cycloalkyl, -(C$_{1i}$-C$_{12}$)-heteroalkyl, -O-(C$_1$-C$_{12}$)-heteroalkyl, -(C$_3$-C$_{14}$) heteroaryl, -O-(C$_3$-C$_1$4)-heteroaryl, -COO-alkyl, -COO-aryl, -C-O-alkyl, C-O-aryl, NH$_2$, and halogen;

wherein the recited alkyl groups, aryl groups, cycloalkyl, heteroalkyl groups and heteroaryl groups may be substituted with:

-(C$_1$-C$_{12}$)-alkyl, -O-(C$^1$-C$_{12}$)-alkyl or halogen; and at least one of the radicals $R^1$, $R^2$, $R^3$ and $R^4$ does not represent phenyl;
   d) introducing to the mixture MeOH;
   e) introducing to the mixture HCOOH, wherein the employed volume of HCOOH based on 2 mmol of olefin is in the range from 0.3 ml to 0.8 ml;
   f) heating of the reaction mixture to convert the olefin, MeOH and HCOOH into the methyl ester where no CO gas is supplied to the reaction mixture.

2. The process according to claim 1, wherein HCOOH serves as the only CO source for the reaction.

3. The process according to claim 1, wherein the compound in process step b) is Pd(acac)$_2$, PdCl$_2$, Pd(dba)$_3$*CH$_3$Cl(dba=dibenzylideneacetone), Pd(OAc)$_2$, Pd(TFA)$_2$, or Pd(CH$_3$CN)Cl$_2$.

4. The process according to claim 1, wherein the process comprises an additional process step g):
   g) adding an acid to the reaction mixture.

5. The process according to claim 4, wherein the acid is H$_2$SO$_4$, CH$_3$SO$_3$H, CF$_3$SO$_3$H, or PTSA.

6. The process according to claim 1, wherein the employed volume of HCOOH based on 2 mmol of olefin is in the range from 0.4 ml to 0.6 ml.

7. The process according to claim 1, wherein $R^1$, $R^2$, $R^3$ and $R^4$ are -(C$_1$-C$_{12}$)-alkyl, -O-(C$_1$-C$_{12}$)- alkyl, -(C$_4$-C$_{14}$)-aryl, -O-(C$_4$-C$_{14}$)-cycloalkyl, -(C$_1$-C$_{12}$)-heteroalkyl, -O-

($C_1$-$C_{12}$)- heteroalkyl, -($C_3$-$C_{14}$)-heteroaryl, -O-($C_3$-$C_{14}$)-heteroaryl, -COO-alkyl, -COO-aryl, -C-O-alkyl, -C-O-aryl, $NH_2$, or halogen;

wherein the recited alkyl groups, aryl groups, cycloalkyl, heteroalkyl groups and heteroaryl groups may be substituted with:

-O-($C_1$-$C_{12}$)-alkyl -O-($C_1$-$C_{12}$)-alkyl or halogen;

and at least one of the radicals $R^2$, $R^3$, $R^2$, and $R^4$ does not represent phenyl.

8. The process according to claim 1, wherein $R^1$, $R^2$, $R^3$ and $R^4$ are -($C_1$-$C_{12}$)-alkyl, -($C_4$-$C_{14}$)-aryl, cycloalkyl, -($C_1$-$C_{12}$)-heteroalkyl, -($C_3$-$C_{14}$)-heteroaryl, or halogen;

wherein the recited alkyl groups, aryl groups, cycloalkyl, heteroalkyl groups and heteroaryl groups may be substituted with as follows:

-($C_1$-$C_{12}$)-alkyl, -O-($C_1$-$C_{12}$)-alkyl or halogen;

and at least one of the radicals $R^1$, $R^2$, $R^3$ and $R^4$ does not represent phenyl.

9. The process according to claim 1, wherein $R^1$, $R^2$, $R^3$ and $R^4$ are -($C_1$-$C_{12}$)-alkyl, cycloalkyl, or -($C_3$-$C_{14}$)-heteroaryl;

wherein the recited alkyl groups, cycloalkyl and heteroaryl groups may be substituted:

with -($C_1$-$C_{12}$)-alkyl, -O-($C_1$-$C_{12}$)-alkyl, halogen, and at least one of the radicals $R^1$, $R^2$, $R^3$ and $R^4$ does not represent phenyl.

10. The process according to claim 1, wherein $R^1$, $R^4$ are -($C_1$-$C_{12}$)-alkyl or cycloalkyl;

wherein the recited alkyl groups and cycloalkyl may be substituted with:

-O -($C_1$-$C_{12}$)-alkyl or halogen.

11. The process according to claim 1, wherein $R^2$, $R^3$ each independently represent -($C_3$-$C_{14}$)-heteroaryl, wherein the recited heteroaryl groups may be substituted with:

-O-($C_1$-$C_{12}$)-alkyl, -O-($C_1$-$C_{12}$)-alkyl or halogen.

12. The process according to claim 1, wherein the compound of general formula (I) has the structure (II):

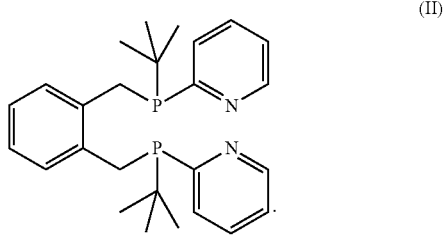

(II)

* * * * *